United States Patent [19]
Robert et al.

[11] 4,176,951
[45] Dec. 4, 1979

[54] ROTATING BIREFRINGENT ELLIPSOMETER AND ITS APPLICATION TO PHOTOELASTICIMETRY

[75] Inventors: André J. Robert, Paris; Claude G. Bourdon, Igny; Nessim C. Msika, Sarcelles; Etienne G. Chorlay, Paris; Jean-Louis Euzenade, St. Michel sur Orge, all of France

[73] Assignee: Etat Francais as represented by the Pelegue General pour l'Armement, Paris, France

[21] Appl. No.: 835,004

[22] Filed: Sep. 20, 1977

[30] Foreign Application Priority Data

Sep. 23, 1976 [FR] France .................. 76 28555

[51] Int. Cl.² .................. G01J 4/04; G01L 1/24
[52] U.S. Cl. .................. 356/33; 356/365
[58] Field of Search .................. 356/33, 34, 116, 117, 356/114, 115, 364, 365, 366, 367, 368

[56] References Cited

U.S. PATENT DOCUMENTS

| 3,738,755 | 6/1973 | Chaney et al. | 356/117 |
| 3,740,151 | 6/1973 | Chaney et al. | 356/117 |
| 3,902,805 | 9/1975 | Redner | 356/116 |
| 3,927,947 | 12/1975 | Kasai | 356/117 |
| 3,988,067 | 10/1976 | Yamamoso et al. | 356/117 |

OTHER PUBLICATIONS

Redner, S. "New Automatic Polariscope System", Experimental Mechanics, vol. 14, No. 12, Dec. 1974, pp. 486-491.

Primary Examiner—John K. Corbin
Assistant Examiner—R. A. Rosenberger
Attorney, Agent, or Firm—Stevens, Davis, Miller & Mosher

[57] ABSTRACT

An ellipsometer for measuring the polarization parameters $\alpha$ and $\lambda$ of an elliptically polarized light wave. The light wave passes successively through an orientable quarter-wave plate, a birefringent plate rotatable at a constant speed $\omega$ and a polarizer and then impinges upon a photodetector. Reference signals having angular frequencies of $2\omega$ and $4\omega$ are generated, one of these signals being employed to synchronously detect the signal at the output of the photodetector by adjusting the quarter-wave plate until the synchronously detected signal component is zero, the orientation of the quarter-wave plate then corresponding to the polarization parameter $\alpha$. The parameter $\lambda$ is obtained by measuring the phase of the component at the output of the photodetector having an angular frequency of $4\omega$.

The invention applies in particular to photoelasticimetry.

21 Claims, 8 Drawing Figures

ROTATING BIREFRINGENT ELLIPSOMETER AND ITS APPLICATION TO PHOTOELASTICIMETRY

BACKGROUND OF THE INVENTION

This invention relates to a rotating birefringent-plate ellipsometer and its application to photoelasticimetry. In other words, the present invention relates to a process and apparatus for analyzing the polarization components of incident light as well as processes and apparatus for determining the characteristics of birefringent media onto which a light beam of known polarization is directed.

In the following description of the prior art and of the present invention, the following concepts will be employed:

(1) Characteristic parameters of the states of polarization of a light wave:

A polarized light wave is, in general, polarized elliptically and, in the limit, it is linearly or circularly polarized. The polarization parameters are $\alpha$ and $\lambda$. $\alpha$ defines the orientation of the major axis of the ellipse with respect to a reference direction, and $\lambda$ defines the flatness of the ellipse. That is, $\lambda$ is equal in absolute value to the ratio of the minor axis of the ellipse to the major axis of the ellipse.

(2) Characteristic parameters of a birefringent plate:

A birefringent plate is defined by the orientation $\theta$ of its fast axis and by the phase shift $\phi$ produced by the plate between the light vectors moving along the fast axis and along the slow axis of the plate respectively.

For example, for circularly polarized light the parameter $\lambda$ is equal to $\pi/4$. If a circularly polarized light beam passes through a birefringent plate of parameters $\theta$ and $\phi$, one will have at the output of the plate:

$$2\alpha = 2\theta - (\pi/2)$$

$$\cos 2\lambda = \sin \phi.$$

Linear light is characterized by the fact that the parameter $\lambda$ is equal to zero. For instance, linear light falling on a birefringent plate of parameters $\theta$ and $\phi$ along the bisectors of the axes of this birefringent will, after having passed through the birefringent, become a light wave characterized by the following parameters $\alpha$ and $\lambda$:

$$\alpha = \theta \pm (\pi/4)$$

$$2\lambda = \phi$$

In the prior art, two principal types of ellipsometers are known; on the one hand, ellipsometers of conventional type in which one proceeds by trying to compensate for an elliptical vibration by means of a variable compensator such as the Babinet compensator, which methods are difficult and lengthy. On the other hand there are automatic processes, such as described in particular in French Pat. No. 1,544,836, and its U.S. counterpart U.S. Pat. No. 3,580,681 in which a polarizer turning in front of a light receiver is employed. Such an automatic apparatus makes it possible to measure $\cos 2\lambda$ and $\alpha$, these parameters corresponding to the amplitude of the alternating part of the electric signal obtained by a photodetector and to the phase of the alternating part. One drawback of this method resides in the fact that one obtains a measure of the cosine of $2\lambda$, and not $\lambda$ directly.

In order to solve this problem, as has been stated in the aforesaid patent, a retractable quarter-wave plate can be added to the unit. The method of use then consists of retracting the quarter-wave plate and measuring $\alpha$ as in the previous case, and then inserting the quarter-wave plate with an orientation corresponding to that of the angle $\alpha$ measured. Thus, the phase of the component having twice the frequency of the frequency of rotation of the rotating analyzer supplies the parameter $\alpha - \lambda$. However, it will be noted that this second method, which permits a measurement of $\lambda$ without passing through a sinusoidal function of this parameter, is relatively complicated.

It will also be noted that, in general, in most of the known ellipsometric, polarimetric and photo-elasticimetric devices, only polarizers (or analyzers), quarter-wave plates and half-wave plates are used for all practical purposes as optical components in measuring apparatus. This is due to the fact that the calculations of the states of polarization of light are simplified considerably in the event specific birefringents are used, such as quarter-wave and half-wave plates. This has had the effect of retarding progress in the field of polarimetry since the various apparatus comprising the three fundamental elements mentioned above were successfully developed. One basis for the present invention resides in the use of a formalism which had been neglected in the field of polarimetry, namely the Poincare sphere formalism. This formalism has been reanalyzed and expanded to make it particularly simple to handle, as set forth in particular in the doctoral thesis of Mr. Andre Robert on Mar. 23, 1973, at the Paul Sabatier University in Toulouse. Thus, as will be shown, the apparatus in accordance with the present invention use any birefringent plates other than quarter-wave or half-wave plates. This constitutes a step forward in polarmetric techniques, in which the use of such elements is not believed to have been contemplated up to the present time.

An object of the present invention is to provide a new ellipsometer which permits direct measurement of the parameters $\alpha$ and $\lambda$ without passing through a trigonometric function of these parameters, this apparatus being particularly simple.

Another object of the present invention is to contemplate applications of such an ellipsometer to photoelastimetric measurements by reflection or transmission.

Still another object is to provide a photoelasticimeter having two wavelengths to permit measurements of the characteristic parameters of a polarized wave or of a birefringent model to be studied while avoiding the indeterminateness within $\pi$ radians which is present in the case of measurements carried out with a single wavelength.

In order to achieve these objects, as well as still other objects, the present invention provides an ellipsometer for the measurement of the polarization parameters $\alpha$ and $\lambda$ of a light wave comprising a birefringent rotating at a constant angular velocity $\omega$; an orientable quarter-wave plate; a polarizer; a photoelectric receiver; means for supplying reference signals of the frequencies $2\omega$ and $4\omega$; electronic means for synchronous detection of the output signals of the receiver having the frequencies $2\omega$ and $4\omega$ in relation to the reference signals, the signal of frequency $2\omega$ being cancelled by the quarter-wave plate, the orientation of which then provides an indication of the first parameter; and means for measuring the phase of the signal of frequency 4ω thereby supplying an indication of the second parameter.

The present invention also provides special arrangements of the components included in the above ellipsometer to permit analysis of the parameters of a model to be studied, the apparatus receiving a light wave of predetermined polarization. It will be noted that one advantage of the present invention is that only phase measurements and no amplitude measurements are effected. One therefore is not hampered by fluctuations in amplitude of the incident light beam and accordingly it is not necessary to provide amplitude control of this beam nor to take precautionary measures with respect to parasitic light.

In the present specification, the letter "ω" is used to designate both frequencies and angular frequencies (pulsations) and the expression "birefringent" as a noun is used to designate an element which exhibits birefringence; for instance, a "rotating birefringent" may designate a mechanically rotating birefringent plate or a Kerr cell subjected to a rotating field.

The objects, advantages, and characteristics of the present invention, and in particular its applications to photoelasticimetry, will be explained in detail in the following description of particular embodiments, given with reference to the accompanying drawings in which.

Figure 1:
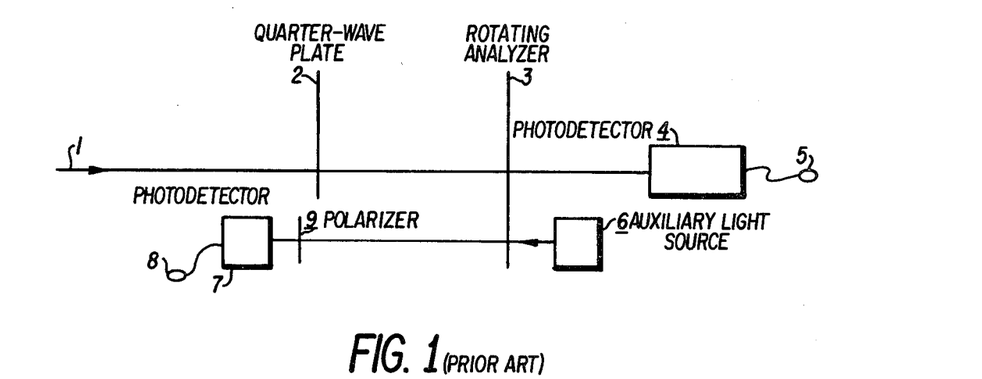
FIG. 1 shows diagrammatically, in block form, an automatic ellipsometer arrangement of the prior art.

In order better to show the novelty and inventive nature of the present invention, there will first be given a brief summary of the nature and operation of an automatic ellipsometer of the prior art with a rotating polarizer, as described for instance in French Pat. No. 1,544,836. The light 1 to be analyzed passes, in succession, through a retractable quarter-wave plate 2 of orientation $\beta$ with respect to a reference direction, through an analyzer (or polarizer) 3 which rotates at a constant velocity of angular frequency ω and then reaches a photodetector 4, which may be a photomultiplier or photodiode supplying output signals to a terminal 5. This apparatus is also provided, in order to supply reference signals, with an auxiliary source of light 6 having a beam which also passes through the rotating analyzer 3 and then through a stationary polarizer 9 before reaching a photodetector 7 which supplies an output signal to a terminal 8.

In the absence of the quarter-wave plate 2, one obtains, at the input of photodetector 4, a light wave whose energy can be expressed by $$E = E_0/2[1 + \cos 2\lambda \cos (2\omega t - \alpha)].$$

Thus, if the alternating component of frequency 2ω is filtered at the terminal 5 from the signal, the measurement of the amplitude of this alternating portion gives $\cos 2\lambda$ and the measurement of the phase gives α, this phase measurement being effected by synchronous detection in relation to the signal obtained at the terminal 8 which is proportional to $\cos 2\omega t$. This arrangement leads to the measurement of an amplitude, and therefrom to amplitude control of the signal received, as explained in detail in the aforementioned patent. Another drawback of this method resides in the fact that the parameter λ is accessible only through the measurement of $\cos 2\lambda$.

A method which makes it possible partially to overcome these drawbacks consists in inserting in the arrangement, as shown in the figure, the retractable and orientable quarter-wave plate 2 after the previous measurement has supplied the value of the parameter α. The quarter-wave plate is inserted with an orientation β corresponding to this value α. There is thus obtained at the terminal 5 a signal whose component of frequency 2ωt is $$\cos 2[\omega t - (\alpha - \lambda)].$$

There is also obtained at the terminal 8 a signal proportional to $\cos 2 (\omega t - \alpha)$ if the signal coming from the source 6 has passed through a polarizer connected to the quarter-wave plate. Synchronous detection between the signals of frequencies 2ωt at the terminals 5 and 8 supplies the value of 2λ directly.

This method of insertion of an orientable quarter-wave plate therefore makes it possible to overcome the two drawbacks mentioned above. However, it increases the difficulty and decreases the speed of the measurement because it is necessary to operate in two steps; that is, first without the quarter-wave plate and then with the quarter-wave plate, the quarter-wave plate being duly oriented as a function of the prior measurement of the parameter α.

These drawbacks are overcome with the ellipsometer in accordance with the present invention, which utilizes a rotating birefringent, as will be described below with respect to one of its embodiments with reference to FIG. 3.

In FIGS. 2a–2c and 3, a beam 10 which is to be analyzed passes, in succession, through an orientable quarter-wave plate 11, a birefringent plate (or birefringent) 12 rotating at a constant angular frequency ω (for instance, by a motor 13) and a polarizer 14. It then strikes a photodetector 15 which supplies electric output signals at a terminal 16. The rotating birefringent is characterized by its phase shift Φ.

At the output terminal 16 of photodetector 15 there is obtained a signal which comprises a constant term, a term in 2ωt, and a term in 4ωt. The term of frequency 2ωt is $$E_{2\omega t} = (E_0/2) \sin \Phi \sin 2\omega t \sin 2(\alpha - \beta) \cos 2\lambda$$

Figure 2A:
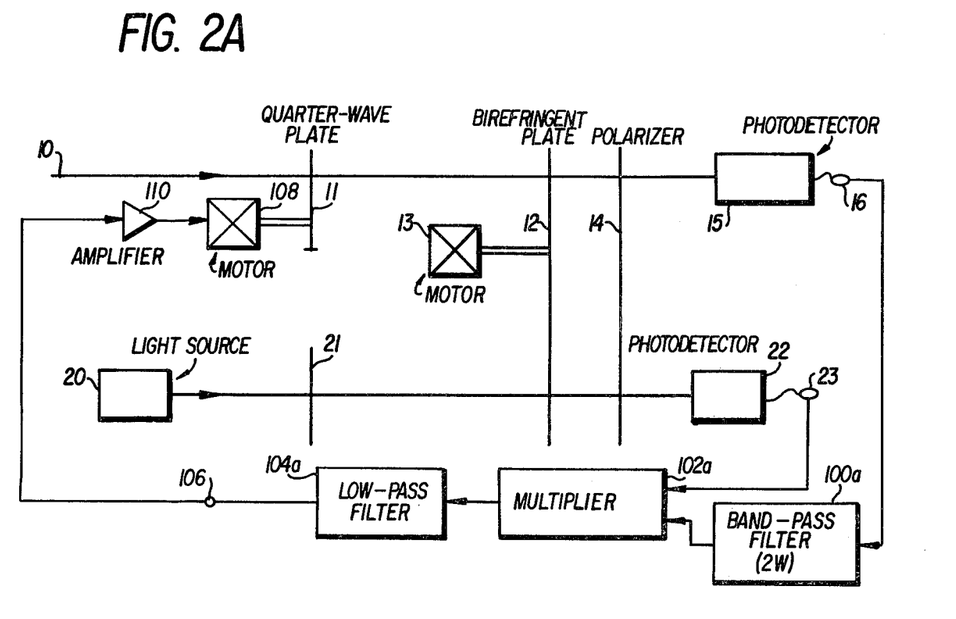
FIGS. 2a, 2b and 2c are block diagrams explaining the operation of the present invention.
Figure 3:
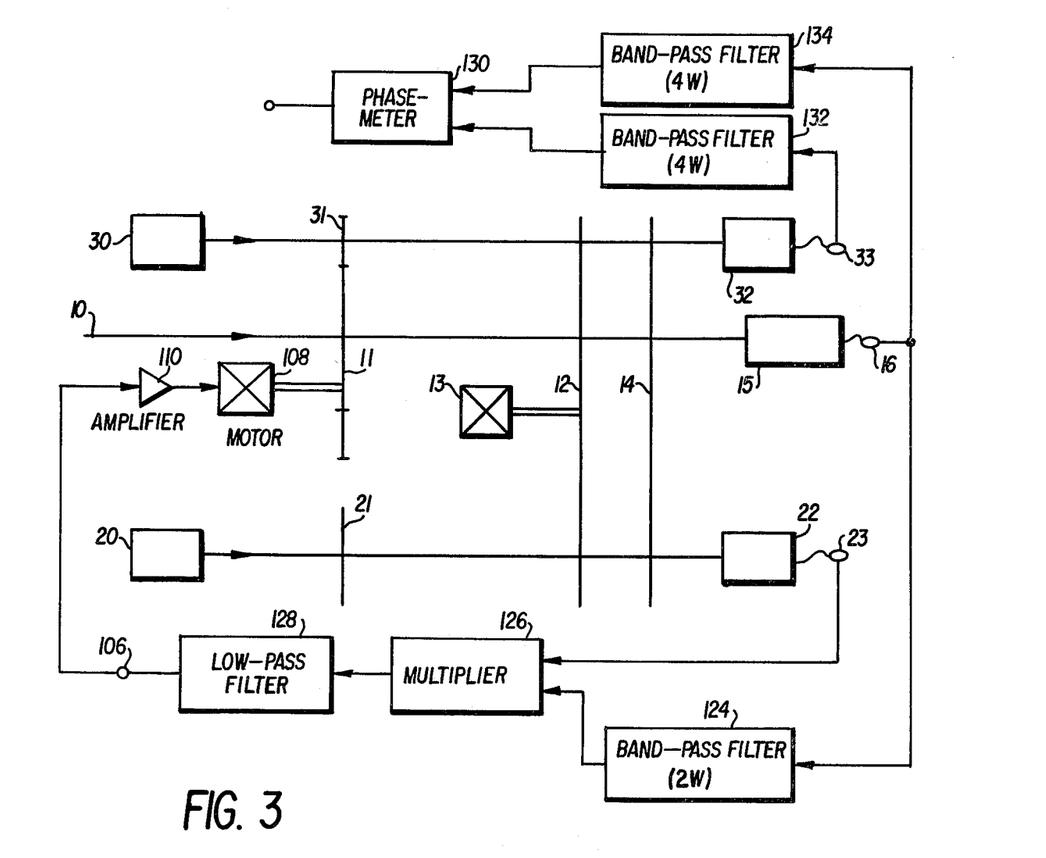
FIG. 3 shows diagrammatically, in block form, an automatic ellipsometer in accordance with the present invention.

In FIGS. 2a and 3, a reference signal having a frequency of 2ωt is generated by a device comprising a source by light 20 having an output beam which passes sequentially through a circular polarizer 21, the rotating birefringent 12 and the stationary polarizer 14 after which it impinges on a photodiode 22 having an output terminal 23. The signal at terminal 23 is proportional to $\sin 2\omega t$ and more precisely to $$(E_0/2) \sin \Phi \sin 2\omega t$$

The signal at terminal 16 of photodetector 15 is filtered in a band-pass filter 100a having a pass band including 2ω and multiplied by the output of photodetector 22 in a multiplier 102a. The output of multiplier 102a is then passed through a low-pass filter 104a which filters the continuous part of the signal at terminal 16 to produce a signal at terminal 106

$$\overline{E_{2\omega t}.\sin 2\omega t} = (E_o/4) \sin \Phi \sin 2(\alpha - \beta) \cos 2\lambda.$$

This continuous term is zero when $\alpha = \beta$ and can be cancelled by adjusting the orientation of the quarter-wave plate of orientation $\beta$. Adjustment of quarter-wave plate 11 is accomplished in FIG. 2a by a motor 108 driven through an amplifier 110 by the output of low-pass filter 104a, motor 108 stopping when the continuous term is zero. A graduated scale (not shown) on quarter-wave plate 11 indicates the value of $2\alpha$ to the nearest integral multiple of $\pi$.

Figure 2B:
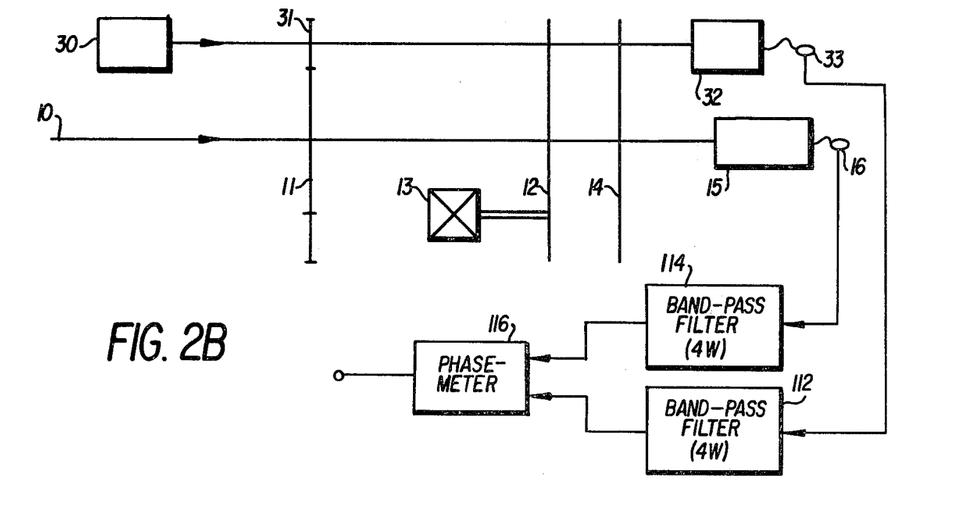

As shown in FIG. 2b, a reference signal proportional to $\cos(4\omega t - 2\beta)$ may be generated by passing light from an auxiliary source 30 sequentially through a polarizer 31 having the same orientation as the quarter-wave plate, the birefringent 12 and the polarizer 14 before striking a photodiode 32 which provides the desired reference signal at an output terminal 33. This reference signal and the output of photodetector 15 are coupled through 4ω band-pass filters 112 and 114 respectively to a phasemeter 16. The frequency component at the output of filter 114 is of the form $$E_{4\omega t} = \frac{E_o(1 - \cos \Phi)}{4} \cdot \cos(4\omega t - 2\beta + 2\lambda).$$

and the frequency component at the output of filter 112 is a reference signal of the form $$E_{4\omega t} = \frac{E_o(1 - \cos \Phi)}{4} \cdot \cos(4\omega t - 2\beta).$$

Consequently, a phase measurement by means of phasemeter 116 gives a direct reading equal to twice the value of the parameter $\lambda$; that is the flatness of the polarization ellipse.

Figure 2C:
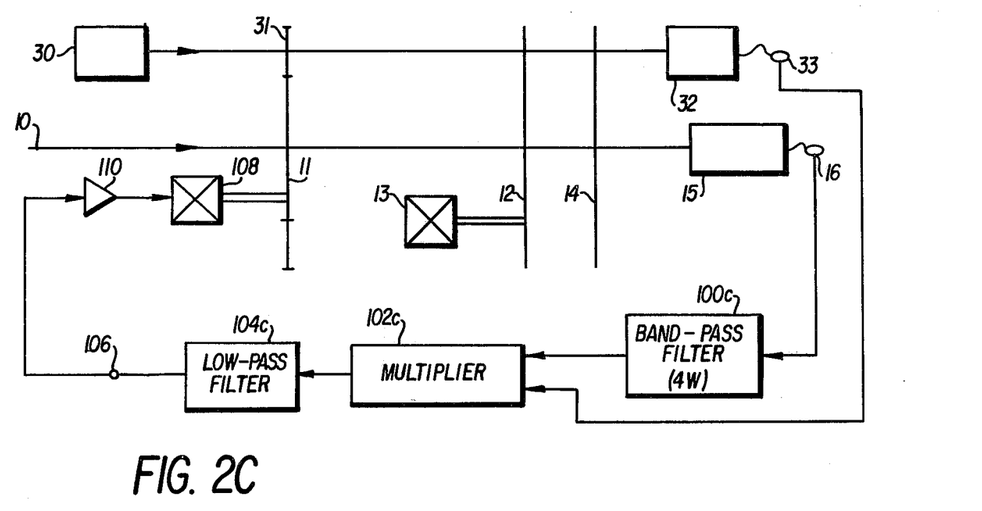

It is also possible to obtain the value of $2\alpha$, as shown in FIG. 2c, by coupling the output of photodetector 15 to a multiplier 102c through a 4ω band-pass filter 100c multiplying this signal by the output of photodetector 32 and filtering the output of multiplier 102c in a low pass filter 104c. The output of filter 104c at terminal 106 is used to drive quarter-wave plate 11 by means of amplifier 110 and motor 108 as explained in connection with FIG. 2a where the 2ω output component of photodetector 15 was used to obtain the value of $2\alpha$.

FIG. 3 shows an ellipsometer for measuring the polarization parameters $\alpha$ and $\lambda$ of an elliptically polarized light wave wherein the parameter $\alpha$ is measured by the method described in connection with FIG. 2a and the parameter $\lambda$ as described in connection with FIG. 2b. In FIG. 3, the output of photodetector 15 is coupled through a 2ω band-pass filter to a multiplier 126 which multiplies it by the output of photodetector 22. The output of multiplier 126 is coupled through a low-pass filter 128 and amplifier 110 to drive motor 108 to a position at which the continuous term at output terminal 106 is zero. Thus, as explained in connection with FIG. 2a, the quarter-wave plate 11 is driven to a position corresponding to the value of $2\alpha$ to the nearest integral multiple of $\pi$.

A phasemeter 130 is coupled through 4ω band-pass filters 132 and 134 to the outputs of photodetectors 15 and 32 respectively. As explained in connection with FIG. 2b, the output of phasemeter 130 will correspond to $2\lambda$.

Thus the use of a rotating birefringent makes it possible to provide an apparatus by which one can obtain, directly by phase measurements, the values of the parameters $\alpha$ and $\lambda$, without regard to the characteristics of the birefringent. It will be noted, however, that this birefringent must not be a strictly half-wave plate, since in such case some of the factors of the signals to be measured and of the reference signals become zero. One interesting case is that in which the birefringent plate is a $3\lambda/4$ plate, since then the factors of most of the electric components become equal. However, this particular selection of the birefringent plate is not necessary, particularly because amplification devices must be provided in the various channels and these amplification devices are controlled independently making it possible to compensate for variations in amplitude between the different signals.

The components shown in FIGS. 2a-2c and 3 are conventional and commercially available. In particular, the multipliers may be type 427J manufactured by Analog Devices, Inc., the filters type UAF 31 commercially available from Burr-Brown Research Corporation and the phasemeter a type 400BN sold by Eurello.

Up to now, there has been described a new apparatus employing a rotating birefringent of any nature whatsoever in order to determine the polarization parameters of a light wave. This ellipsometer may be used directly in transmission or reflection elasticimetry by sending a light beam of known polarization to a point of a model to be studied and analyzing the parameters $\alpha$ and $\lambda$ of the outgoing light wave from the model with the ellipsometer described above. As the incident light wave on the model has known polarization parameters, the relations between the parameters $\alpha$ and $\lambda$ supplied by the ellipsometer and the birefringence parameters $\theta$ and $\phi$ of the model at the point in question can be easily calculated and the values of $\theta$ and $\phi$ can be deducted from the values of $\alpha$ and $\lambda$. Nevertheless, certain special arrangements will be described below which permit direct measurement of the parameters $\theta$ and $\phi$ in a particularly simple manner.

Figure 4:
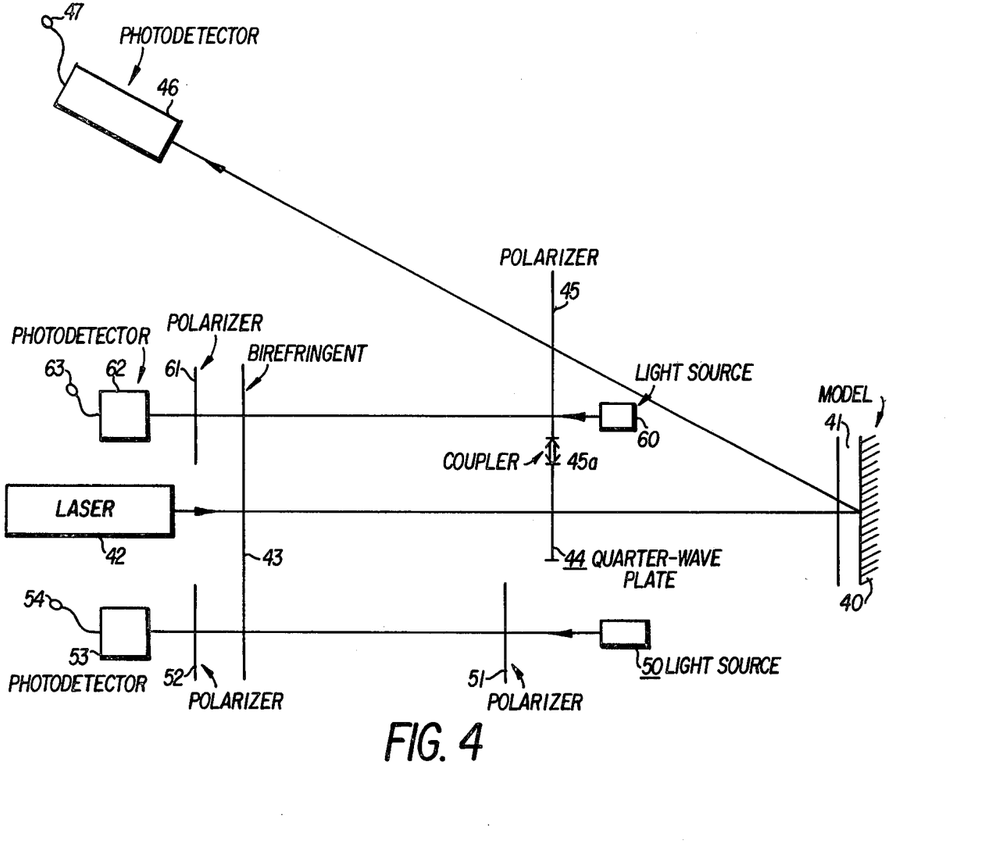
FIG. 4 shows diagrammatically, in block form, a reflection photoelasticimeter in accordance with the present invention.
Figure 6:
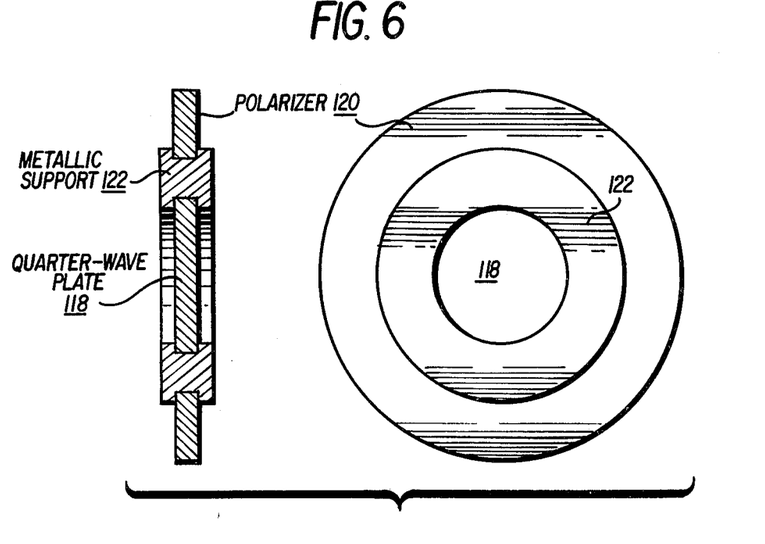
FIG. 6 illustrates an annular polarizer.

FIG. 4 shows a photoelasticimeter for measuring the parameters $\theta$ and $\phi$ relating to an opaque model 40 under stress which is provided with a suitable varnish 41 and which is studied in reflection. In this case, the light source is a laser 42 whose outgoing beam passes, in succession, through a birefringent 43 rotating at constant velocity and characterized by a phase shift $\Phi$ which it imparts to the light waves moving along its major axis and its minor axis respectively, an orientable quarter-wave plate 44 forming an angle $\beta$ with one reference direction, the varnish 41 on which it is reflected, and a polarizer 45 which is orientable in agreement with the quarter wave plate 44, and forms the same angle $\beta$ with respect to a reference direction. This beam then reaches a photodetector 46 supplying an electric signal at its output terminal 47. The quarter-wave plate 44 and the polarizer 45 can be connected for instance by gearing 45a or, as shown in FIG. 6, may be in the form of a central part 118 formed of a quarter-wave plate and an annular part formed of a polarizing plate 120 separated from the quarter-wave plate by a metallic support 122.

The output signal obtained at the terminal 47 comprises continuous components, components of frequency $2\omega$ and components of frequency $4\omega$. After filtration of the frequency $2\omega$ and multiplication by sin $2\omega t$, in the manner disclosed in FIG. 2a, the component of frequency $2\omega$ becomes:

$$\overline{E_{2\omega t} \sin 2\omega t} = (E_o/4) \sin \Phi \sin 2(\theta - \beta)(1 - \cos \phi).$$

By turning the orientable quarter-wave plate 44 and at the same time the polarizer 45 it will be noted that the above signal can be cancelled out as follows:
For $\cos 2(\theta - \beta) = 0$; $\theta = \beta + k \pi/4$ $(k = \pm 1)$
For $\sin 2(\theta - \beta) = 0$; $\theta = \beta$ or $\theta = \beta + \pi/2$ One can thus also measure the angle $\theta$ as a function of the angle $\beta$ measured on the quarter-wave plate or the polarizer. Nevertheless, there remains an indeterminateness as to the value of $\theta$. This indeterminateness can be removed by considering the signal of frequency $4\omega$.

In the event $\sin 2(\theta - \beta) = 0$, the $4\omega t$ frequency signal is $$E_{4\omega t} = (E_o/4)(1 - \cos \Phi) \cos (4\omega t - 2\beta).$$

This signal does not depend on the characteristic phase $\phi$ of the model and is in phase with a reference signal which can be obtained as described hereinafter $$(E_{4\omega t})_{REF} \text{ proportional to } \cos (4\omega t - 2\beta),$$

in which case $\sin 2(\theta - \beta) = 0$ can easily be eliminated for observation of the signal $4\omega t$. In the event $\cos 2(\theta - \beta) = 0$; that is, $$\theta = \beta + k\pi/4 (k = \pm 1),$$

the signal in $4\omega t$ is written:

$$E_{4\omega t} = (E_o/4)(1 - \cos \Phi) \cos (4\omega t - 2\beta - k\phi)$$

A phase measurement between this signal and a reference signal of $\alpha(4\omega t - 2\beta)$ therefore supplies k $\Phi$; that is, the sign and the amplitude of $\phi$. It will be noted that the indeterminateness as in the value of $\theta$ has been removed by cancelling out the $2\omega$ frequency channel when the phase $\Phi$ is maximum. As a matter of fact, in the adjustment which it is desired to eliminate for which $\sin 2(\theta - \beta) = 0$, there is found a zero value for the phase $\phi$. One then has $\theta = \beta + k\pi/4$, the sign of k being also determined.

Referring again to FIG. 4, the reference signal in $2\omega t$ can be obtained by using a light source 50 whose beam passes, in succession, through a circular polarizer 51, the rotating birefringent 43, and a stationary polarizer 52, before reaching a photodiode 53, which provides a signal at its output terminal 54 of the form:

$$(E_{2\omega t})_{REF} = (E_o/2) \sin \Phi \sin 2\omega t.$$

The reflection photoelasticimeter described in connection with FIG. 4 can be adapted directly to provide a transmission photoelasticimeter. In this case, the laser, the rotating birefringent, the quarter-wave plate, the polarizer and the photodiode are placed in line. The model to be studied is inserted between the quarter-wave plate and the polarizer. It will be noted that it is necessary to provide a coupling other than the simple mechanical coupling 45a provided in the case of FIG. 3 between the quarter-wave plate 44 and the polarizer 45 so that these two parts will constantly have the same orientation. This coupling can, for instance, be a mechanical coupling or an electrically controlled coupling.

Another application of the ellipsometer in accordance with the present invention resides in its adaptation to a photoelasticimeter having two wavelengths.

It has been noted previously that the various parameters of a form of light or of a birefringent to be analyzed were given with a certain indeterminateness to the extent of a factor $k\pi$. In the event these parameters assume values of more than $\pi$, this indeterminateness can be removed by making the measurements for two different incident wavelengths as is known in the prior art.

It will be noted below that an elasticimeter in accordance with the present invention is particularly well adapted to such an analysis in two wavelengths and has in particular the advantage over the prior art devices that it permits operation with a laser source and not with spread beams, as was done in the prior art.

Figure 5:
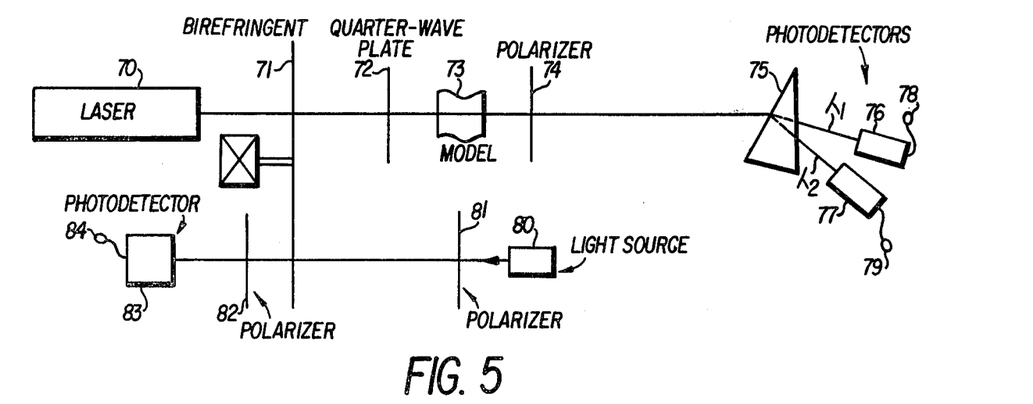
FIG. 5 shows diagrammatically, in block form, an automatic multiple-wavelength photoelasticimeter in accordance with the present invention.

FIG. 5 shows an embodiment of such a two wavelength photoelasticimeter. A polarized laser source 70 with two wavelengths $\lambda_1$ and $\lambda_2$ sends out a light beam which passes in succession through a birefringent 71 rotating at constant speed $\omega$, an orientable quarter-wave plate 72 of orientation $\beta$, a model to be studied 73 and a polarizer 74 of the same orientation $\beta$ as the quarter-wave plate 72. The beam emerging from the polarizer is transmitted via a dispersion means such as a prism 75 so as to be separated spatially and send the light beams of wavelengths $\lambda_1$ and $\lambda_2$ towards photo-receivers 76 and 77, respectively provided with output terminals 78 and 79. The quarter-wave plate must be substantially a quarter-wave for the two wavelengths selected. It is found in fact that it is sufficient that it be a quarter-wave for the average value of the two wavelengths, and that the resultant error is negligible. The signals at the terminals 78 and 79 comprise continuous components of frequency $2\omega$ and frequency $4\omega$.

The signals of frequency $2\omega$ are given for the wavelength $\lambda_1$ by the expression:

$$(E_{2\omega t})_1 = \frac{E_o}{2} \sin \Phi_1 \sin 2 (\theta - \beta) \cos 2 (\theta - \beta)$$
$$(1 - \cos \phi_1) \sin 2\omega t$$

and for the wavelength $\lambda_2$ by the expression:

$$(E_{2\omega t})_2 = \frac{E_o}{2} \sin \Phi_2 \sin 2 (\theta - \beta) \cos 2 (\theta - \beta)$$
$$(1 - \cos \phi_2) \sin 2\omega t$$

The sum of the two signals $(E_{2\omega t})_1$ and $(E_{2\omega t})_2$ multiplied by $\sin 2\omega t$ presents a continuous component which is proportional to $$\cos 2(\theta - \beta) \sin 2(\theta - \beta),$$

the coefficient of which is always positive. By changing the orientation of the quarter-wave plate it is possible to cancel out this error term. The quarter-wave plate is then oriented either along the fast axis of the birefringent formed by the model at the point in question or along the bisectors of the axes of the birefringent formed by the model to be studied. It is then possible to control the position of the fast axis of the quarter-wave plate in such a manner that it is oriented along the bisectors of the axes of the birefringent under study. For this, known methods are used taking into account the fact that the signal is cancelled with a positive slope or a negative slope depending on whether one is along the fast axis or along the bisectors. One then has $\theta = \beta + k(\pi/4)$ in which $k = \pm 1$.

As will be seen below, this indeterminateness as to the value of k will be removed in a manner similar to the case previously described in connection with FIG. 3 when considering the term in $4\omega t$. This term in $4\omega t$ taken from the output of the terminals 78 and 79 after filtration at the angular frequency $4\omega$ is equal to:

$$(E_{4\omega t})_{1,2} = \frac{E_{o1,2}}{4} (1 - \cos \Phi_{1,2}) \cos (4\omega t - 2\beta - k \phi_{1,2})$$

in which the expression 1,2 designates the subscript to be applied depending on whether one is in the channel corresponding to the length $\lambda_1$ or that corresponding to $\lambda_2$.

At the point in question of the model, the average phase shift $\phi_m$ relative to the average wavelength $\lambda_m = (\lambda_1 + \lambda_2)/2$ is written:

$$\phi_m = \frac{\lambda_m}{\Delta\lambda} (\phi_2 - \phi_1) \text{ with } \Delta\lambda = \lambda_1 - \lambda_2 \text{ and } \lambda_1 > \lambda_2$$

The difference in phase shift between the two signals $(E_{4\omega t})_1$ and $(E_{4\omega t})_2$ supplies the value of $k(\phi_2 - \phi_1)$. The advance or delay of the phase $\phi_2$ with respect to $\phi_1$ gives the sign of k. The phase shift $\phi_2 - \phi_1$ is therefore known together with its sign, with the result that one can determine the phase shift $\phi_m$ for $\lambda_m$ as well as the orientation of the fast axis of the birefringent formed by the model at the point in question $\theta = \beta + k\pi/4$.

It will be noted that in this particular case of a photoelasticimeter with two wavelengths, it is not necessary to provide a reference signal of frequency $4\omega$ but only a reference signal of frequency $2\omega$ which can be obtained as shown in FIG. 4 by means of a light source 80 which sends a beam through a circular polarizer 81, the rotating birefringent 71, and a polarizer 82 towards a photodetector 83 provided with an output terminal 84. The signal at this output terminal is $$(E_{2\omega t})_{REF} = (E_o/2) \sin \Phi \sin \omega t.$$

It will be noted that the two photoelasticimeters represented in FIGS. 4 and 5 constitute only special cases of application of the ellipsometer described in general in connection with FIG. 3 and employing in particular a birefringent rotating at constant velocity. It should again be emphasized that one of the advantages of the present invention resides in the fact that only phase measurements are used and not amplitude measurements as in the case of numerous methods of the prior art. The result is that fewer precautions need be taken in the measurements which classically are very delicate. There will be noted in particular, in addition to the advantages cited above, the arrangement shown in FIG. 4 in which the quarter-wave plate 44 and the polarizer 45 which are in the same plane are traversed by nonparallel beams, which does not correspond to their optimal use and must be avoided in the practical cases of the prior art. Due to the fact that only phases are measured, such an arrangement can be used without drawback in the present invention.

In all the examples described, the source of light was a laser but of course it can be any substantially monochromatic conventional source; however, it will then be necessary to provide suitable focusing and combining means. It will also be noted that the sources intended for the supply of reference signals will have substantially the same color as the source of the principal analysis beam.

Furthermore, in the examples of FIGS. 2a-2c, 3, 4 and 5, there have been indicated special arrangements for obtaining reference signals but of course these are merely examples and numerous other arrangements can be devised by the person skilled in the art. One or more known digital or analog display and/or recording means may be used to provide the user of the apparatus with the values of the parameters $\alpha$ and $\lambda$ or $\theta$ and $\phi$ sought.

The present invention is not limited to the embodiments which have been described but is capable of variations and modifications which will be evident to the person skilled in the art.

We claim:

1. An ellipsometer for measuring the polarization parameters $\alpha$ and $\lambda$ of an elliptically polarized light wave wherein $\alpha$ corresponds to the orientation of the major axis of the ellipse with respect to a reference direction and $\lambda$ corresponds to the flatness of the ellipse, comprising
    an orientable quarter-wave plate having an orientation $\beta$,
    a birefringent plate rotatable at a constant angular speed $\omega$,
    a first polarizer,
    a first photodetector for receiving said light wave and generating signal components having angular frequencies of $2\omega$ and $4\omega$, said light wave traversing said quarter-wave plate, said birefringent plate and said polarizer before impinging on said first photodetector,
    first and second reference signal generating means for generating signals having angular frequencies of $2\omega$ and $4\omega$ respectively,
    synchronous detection means coupled to said first photodetector and to one of said first and second reference signal generating means for synchronously detecting the signal components at the output of said first photodetector, said polarization parameter $\alpha$ being obtained by adjusting said quarter-wave plate until the synchronously detected signal component is reduced to zero, the orientation of said quarter-wave plate then corresponding to $\alpha$, and,
    phase measuring means coupled to said first photodetector and said second reference signal generating means for measuring the phase of the component at the output of said first photodetector having an angular frequency of $4\omega$, said phase corresponding to the polarization parameter $\lambda$.

2. An ellipsometer as defined by claim 1 wherein said first reference signal generating means comprises in succession a circular polarizer, said rotatable birefringent plate, said first polarizer and a second photodetector, light produced by an auxiliary light source passing through said successive elements to impinge on said second photodetector to generate said signal having an angular frequency of $2\omega$.

3. An ellipsometer as defined by claim 2 which further comprises means coupled to the output of said synchronous detection means for rotating said quarter-wave plate until the component of angular frequency of $2\omega$ at the output of said first photodetector is zero.

4. An ellipsometer as defined by claim 2 wherein said second reference signal generating means comprises in succession an auxiliary polarizer having the same orientation $\beta$ as said quarter-wave plate, said rotatable birefringent plate, said first polarizer and a third photodetector, light produced by an auxiliary light source passing through said successive elements to impinge on said third photodetector to generate said signal having an angular frequency of $4\omega$.

5. An ellipsometer as defined by claim 4 wherein said quarter-wave plate is mounted integrally with said auxiliary polarizer, said auxiliary polarizer being annular and surrounding said quarter-wave plate.

6. An ellipsometer as defined by claim 1 wherein said second reference signal generating means comprises in succession an auxiliary polarizer having the same orientation as said quarter-wave plate, said rotatable birefringent plate, said first polarizer and a third photodetector, light produced by an auxiliary light source passing through said successive elements to impinge on said third photodetector to generate said signal having an angular frequency of $4\omega$.

7. An ellipsometer as defined by claim 6 wherein said quarter-wave plate is mounted integrally with said auxiliary polarizer, said auxiliary polarizer being annular and surrounding said quarter-wave plate.

8. An ellipsometer as defined by claim 1 which further comprises means coupled to the output of said synchronous detection means for rotating said quarter-wave plate until the component of angular frequency of $2\omega$ at the output of said first photodetector is zero.

9. An ellipsometer as defined by claim 1 wherein said synchronous detection means comprises a first band-pass filter coupled to the output of said first detector, a multiplier coupled to the output of said first band-pass filter and to one of said first and second reference signal generating means, and a low-pass filter coupled to the output of said multiplier.

10. An ellipsometer as defined by claim 9 wherein said first band-pass filter transmits an angular frequency of $2\omega$ and said multiplier is coupled to said first reference signal generating means.

11. An ellipsometer as defined by claim 9 wherein said first band-pass filter transmits an angular frequency of $4\omega$ and said multiplier is coupled to said second reference signal generating means.

12. An ellipsometer as defined by claim 9 wherein said phase measuring means comprises second and third band-pass filters, each transmitting an angular frequency of $4\omega$, coupled to said first photodetector and to said second reference signal generating means respectively, and a phasemeter coupled to the outputs of said second and third band-pass filters.

13. An ellipsometer as defined by claim 1 wherein said phase measuring means comprises second and third band-pass filters, each transmitting an angular frequency of $4\omega$, coupled to said first photodetector and to said second reference signal generating means respectively, and a phasemeter coupled to the outputs of said second and third band-pass filters.

14. A photoelasticimeter for measuring the birefringent parameters $\theta$ and $\phi$ of a model at a point under study, comprising in succession a birefringent plate rotatable at a constant angular speed $\omega$,
an orientable quarter-wave plate having an orientation $\beta$,
a polarizer having the same orientation $\beta$ as said quarter-wave plate, said model being located between said quarter-wave plate and said polarizer,
a first photodetector,
first and second reference signal generating means for generating first and second reference signals having angular frequencies of $2\omega$ and $4\omega$ respectively,
synchronous detection means for detecting the signal components at the output of said first photodetector having angular frequencies of $2\omega$ and $4\omega$ with respect to said first and second reference signals,
means for varying the orientation of said quarter-wave plate and said polarizer to cancel the component of the signal having an angular frequency of $2\omega$ when the component of the signal having a frequency of $4\omega$ is maximum, the orientation $\beta$ of said quarter-wave plate being then related to the parameter $\theta$ by the relationship $\theta = \beta + k\pi/4$; and
means for measuring the phase of the signal having an angular frequency of $4\omega$ thereby providing a signal corresponding to the parameter $\theta$ and the sign of k ($\pm 1$).

15. A photoelasticimeter as defined by claim 14 wherein said model is transparent and said quarter-wave plate and said polarizer are coupled together.

16. A photoelasticimeter as defined by claim 14 wherein the light coming from said quarter-wave plate is reflected from said model before striking said polarizer, and wherein said quarter-wave plate is mounted integrally with said polarizer, said polarizer being annular and surrounding said quarter-wave plate.

17. A photoelasticimeter as defined by claim 14 wherein said first reference signal generating means comprises in succession a circular polarizer, said rotatable birefringent plate, an auxiliary polarizer and a second photodetector, light produced by an auxiliary light source passing through said successive elements to impinge on said second photodetector to generate said signal having an angular frequency of $2\omega$.

18. A photoelasticimeter as defined by claim 14 wherein said second reference signal generating means comprises in succession said orientable quarter-wave plate, said rotatable birefringent plate, an auxiliary polarizer and a third photodetector, light produced by an auxiliary light source passing through said successive elements to impinge on said third photodetector to generate said signal having an angular frequency of $4\omega$.

19. A photoelasticimeter for measuring the polarization parameters $\theta$ and $\phi$ of a model at a point under study, comprising
a source of light emitting a light wave having at least two wavelengths $\lambda_1$ and $\lambda_2$,
a birefringent plate rotatable at a constant angular speed $\omega$,
an orientable quarter-wave plate having an orientation $\beta$,
a polarizer having an orientation $\beta$, said model being located between said quarter-wave plate and said polarizer,
dispersion means for spatially separating beams of wavelengths $\lambda_1$ and $\lambda_2$,
first and second photodetectors for receiving signals having wavelengths of $\lambda_1$ and $\lambda_2$, respectively, reference signal generating means for generating a reference signal having an angular frequency of 2ω, synchronous detection means for detecting signals having a frequency of 2ω generated by said first and second photodetectors with respect to said reference signal, means for adding and filtering the continuous components of said signals, means for modifying the orientation of said quarter-wave plate and said polarizer thereby cancelling said continuous component for determination of the parameter θ, means for filtering the signals generated by first and second photodetectors to obtain signals having an angular frequency of 4ω, and means for measuring the difference in phase shift between said signals having a frequency of 4ω for determining the parameter θ.

20. The photoelasticimeter as defined by claim 19 wherein said source of light is a laser emitting at least two wavelengths.

21. A photoelasticimeter as defined by claim 19 wherein said reference signal generating means comprises in succession a circular polarizer, said rotatable birefringent, an auxiliary polarizer and a third photodetector, light produced by an auxiliary light source passing through said successive elements to impinge on said third photodetector to generate said reference signal having an angular frequency of 2ω.

* * * * *